(12) United States Patent
Kraft et al.

(10) Patent No.: US 8,334,392 B2
(45) Date of Patent: Dec. 18, 2012

(54) PROCESS FOR THE PRODUCTION OF ARTEMISININ INTERMEDIATES

(75) Inventors: Volker Kraft, Frankfurt (DE); Gerhard Kretzschmar, Frankurt (DE); Kai Rossen, Frankfurt (DE)

(73) Assignee: Sanofi, Paris (FR)

( * ) Notice: Subject to any disclaimer, the term of this patent is extended or adjusted under 35 U.S.C. 154(b) by 288 days.

(21) Appl. No.: 12/879,241

(22) Filed: Sep. 10, 2010

(65) Prior Publication Data

US 2011/0230669 A1    Sep. 22, 2011

Related U.S. Application Data

(60) Provisional application No. 61/241,744, filed on Sep. 11, 2009.

(51) Int. Cl.
*C07D 311/78* (2006.01)
(52) U.S. Cl. ...................................... 549/276
(58) Field of Classification Search ............... 549/276
See application file for complete search history.

(56) References Cited

U.S. PATENT DOCUMENTS

| | | | |
|---|---|---|---|
| 4,992,561 | A | 2/1991 | Roth et al. |
| 5,872,273 | A | 2/1999 | Saito et al. |
| 5,955,084 | A | 9/1999 | Jain et al. |
| 6,313,317 | B1 | 11/2001 | Sayo et al. |

FOREIGN PATENT DOCUMENTS

| | | |
|---|---|---|
| IN | 184682 | 9/2000 |
| WO | WO 2006/128126 | 11/2006 |
| WO | WO 2009/088404 A1 | 7/2009 |

OTHER PUBLICATIONS

Hung et al. Angewandte Chemie, 1965, 4, 271-280.*
B.E. Cross, J.Chem. Soc. (London), 1960, 3022-3038.*
International Search Report and Written Opinion mailed on Dec. 9, 2010, for International Application No. PCT/EP2010/062811, filed on Sep. 1, 2010.
Imada et al., "Flavin-Catalyzed Generation of Diimide: An Environmentally Friendly Method for the Aerobic Hydrogenation of Olefins," *Journal of the American Chemical Society*, 2005, vol. 127, No. 42, pp. 14544-14545.
International Search Report and Written Opinion of the International Searching Authority for PCT/IB2010/002566 mailed on Mar. 16, 2011.
Abdin et al., Artemisinin, a novel antimalarial drug: biochemical and molecular approaches for enhanced production. *Planta Med* 2003, 69(4), 289-99.
Greene et al., Protective Groups in Organic Synthesis; Wiley-Interscience 3$^{rd}$ ed., chapter 5 (1999).
Jung et al., A concise and stereoselective synthesis of (+)-12-butyldeoxoartemisinin, *Synlett* 1990, 12, 743-744.
Liu et al., "A Total Synthesis of the Antimalarial Natural Product (+)-Qinghaosu," *Tetrahedron Letters*, 1993, 34(28), 4435-4438.
Miyashita et al., Synthesis of 2,2'-bis(diphenylphosphino)-1,1'-binapthyl(BINAP), an atropisomeric chiral bis(triaryl)phosphine, and its use in the rhodium(I)-catalyzed asymmetric hydrogenation of α-(acylamino)acrylic acids. *J. Am. Chem. Soc.* 1980, 102(27), 7932-7934.
Pasto and Taylor, Reduction with diimide. L.A. Paquette, Editor, Organic Reactions vol. 40, John Willey and Sons, Inc., New York (1991), pp. 91-155.
Lenihan et al., Developing an industrial artemisinic acid fermentation process to support the cost-effective production of antimalarial artemisinin-based combination therapies. *Biotechnol Prog.* 2008, 24(5), 1026-32.
Ro et al., Production of the antimalarial drug precursor artemisinic acid in engineered yeast. *Nature* 2006, 440(7086), 940-3.
Roth et al., Isolation of arteannuic acid from *Artemisia annua. Planta Med* 1987, 53(5), 501-2.
Schmid and Hofheinz, Total synthesis of qinghaosu. *J. Am. Chem. Soc.* 1983, 105, 624-625.
Wallaart et al., Seasonal variation of artemisinin and its biosynthetic precursors in plants of *Artemisia annua* of different geographical origin: proof for the existence of chemotypes. *Planta Med* 2000, 66(1), 57-62.
Wei-Shan et al., Studies on the structures and synthesis of arteannuin and related compounds: XVI. Synthesis of arteannuin E and epoxy fission reaction of methyl α-epoxy arteannuinate. *HuexueXuebao (Acta Chimica Sinica)* 1985, 43(9), 845-851.
Xu et al., Total synthesis of arteannuin and deoxyarteannuin. *Tetrahedron* 1986, 42(3), 819-828.
European Search Report dated Feb. 9, 2010, issued in European Application No. 09305805.5, 5 pages.
U.S. Appl. No. 12/873,925, filed Sep. 1, 2010.

* cited by examiner

*Primary Examiner* — Nizal Chandrakumar
(74) *Attorney, Agent, or Firm* — Finnegan, Henderson, Farabow, Garrett & Dunner, LLP

(57) ABSTRACT

This application relates to a process for the production of (2R)-dihydroartemisinic acid or (2R)-dihydroartemisinic acid esters from artemisinic acid or artemisinic acid esters, respectively, by diimine hydrogenation of the exocyclic CC-double bond, and use of said process in the production of the antimalarial drug artemisinin.

7 Claims, No Drawings

PROCESS FOR THE PRODUCTION OF ARTEMISININ INTERMEDIATES

This application claims the benefit under 35 U.S.C. §119 of U.S. Provisional Application Ser. No. 61/241,744, filed Sep. 11, 2009, which is incorporated by reference in its entirety.

Malaria is a tropical disease and is common in Africa, South East Asia and South America. Approximately 300-500 million people are infected with malaria, making it one of the world's major infectious diseases. In 2006, an estimated 1.5 to 2.7 million deaths resulted from malaria and most of the deaths occurred in children under five years old. Disease control is hampered by the occurrence of multi-drug resistant strains of the parasite *Plasmodium falciparum*. Therefore it is an important world health objective to develop new anti-malaria drugs, and alternative methods of producing anti-malaria drugs. One of these anti-malaria drugs is artemisinin of the formula II,

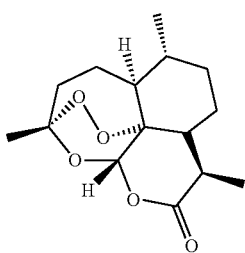

II a sesquiterpene lactone endoperoxide which is a component of the traditional Chinese medical herb *Artemisia annua*. It has been utilized for controlling symptoms of fever in China for over 1000 years. In the scientific literature, artemisinin is also sometimes referred to by its Chinese name Qinghaosu. Recent strides have been made in understanding the properties and structure of this molecule. The compound was first isolated in 1972. Its anti-malaria activity was discovered in 1979. The first total synthesis of the molecule was accomplished by chemists at Hoffmann-La Roche in 1983 (G. Schmidt, W. Hofheinz, J. Am. Chem. Soc., 105, 624 (1983)). Artemisinin is highly effective against multi-drug resistant *Plasmodium* spp., but is in short supply and unaffordable to most malaria sufferers. The production of artemisinin can be accomplished through several routes. One method involves extracting artemisinin from *Artemisia annua*. A drawback of this method is the low and inconsistent yields (0.001-0.8%) of artemisinin from the plant (Wallaart et al., Planta Med; 66, 57 (2000); Abdin et al., Planta Med; 69, 289 (2003)).

An alternate preparation procedure for artemisinin involves extracting the biosynthetic precursor molecule artemisinic acid of formula IIIa,

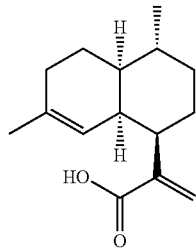

IIIa from *Artemisia annua* and then synthetically converting this molecule in several synthetic steps into artemisinin. Because the acid of formula IIIa can be present in *Artemisia annua* at levels approximately 10 times higher than artemisinin, the conversion of the former into the antimalarial drug has received a great deal of attention. However, the yields of compound IIIa from *Artemisia annua* are variable and despite the quick growth of *Artemisia annua*, it is currently estimated that the world's supply of the plant would meet less than 10% of the world's demand for artemisinic acid and artemisinin (WO 2006/128126).

Another alternate production procedure is the total synthesis of artemisinin. However, such total synthesis involves a large number of synthetic steps and is not efficient and cost-effective in order to provide large amounts of the desired drug.

On the other hand, its semi-synthesis from a valuable bio-synthetic precursor like artemisinic acid of the formula IIIa, to be produced by fermentation of a genetically engineered microorganism, could be a cost-effective, environmentally friendly, high quality and reliable source of artemisinin. A major breakthrough to this end has been achieved by scientists from Amyris Inc. and the University of California, Berkeley in 2006 who developed a fermentation process with engineered yeast producing high titres of artemisinic acid of the formula IIIa using an engineered mevalonate pathway, amorphadiene synthase, and a novel cytochrome P450 monooxygenase from *Artemisia annua* that performs a three step oxidation of amorpha-4,11-diene to the intermediate of formula IIIa (J. D. Keasling et al., Nature, 440, 940 (2006)). Two years later, the titres are being increased to even higher and even more economical levels (R. Regentin et al., Biotechnol. Prog.; 24, 1026 (2008)).

The regio- and stereoselective reduction of artemisinic acid or artemisinic acid esters may be performed using the following methods:

a) The reduction with lithium boron hydride ($LiBH_4$) and nickel chloride ($NiCl_2$), a reagent combination often referred to as nickel boride, generates a mixture of the desired diastereomeric dihydroartemisinic acid or dihydroartemisinic acid ester (2R)-isomer I and the undesired (2S)-isomer IV,

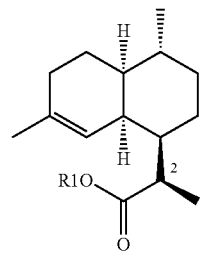

I

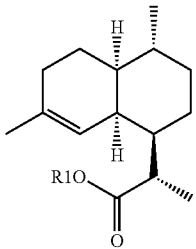

IV in a ratio of 85:15, which is insufficient stereoselectivity (X. Xu et al., Tetrahedron; 42, 819 (1986)). In addition, quite a large excess of the hydride reagent is required, which makes handling and workup procedures difficult on a large scale.

Furthermore, the reduction method is restricted to the compounds of the formula III wherein R1 is not H, and has not been described to be amenable to the free acid of the formula IIIa (see WO 2006/128126). In an earlier work complete stereoselectivity for this transformation has been reported (M. Jung et al.; Synlett; 74 (1990)), however, the high diastereoselectivity could not be reproduced and confirmed later on by others (see WO 2006/128126). In fact, the product ratio did not exceed the results from the nickel boride reduction. Some modifications of this procedure suffering from the same drawbacks as described above were also described (for example by R. J. Roth et al., U.S. Pat. No. 4,992,561).

b) The regio- and diastereoselective homogeneous catalytic hydrogenation, which has been developed by Knowles and Noyori (W. S. Knowles et al., J. Am. Chem. Soc., 99, 5946 (1977); R. Noyori et al., J. Am. Chem. Soc., 102, 7932 (1980)) makes use of a transition metal catalyst, which may be chiral, to achieve the diastereo- or enantio-selective hydrogenation of an alkene, respectively. For instance, K. Reiling et al. (WO 2006/128126) performed the desired conversion of the acid of formula IIIa into the acid of formula Ia (i.e., a compound of the formula I wherein R1 is hydrogen) by using an achiral rhodium-based Wilkinson-type catalyst to give a mixture of the (2R)/(2S)-stereoisomers with a ratio of only 85:15. Homogenous catalytic hydrogenation using transition metal complexes are, however, extremely costly in view of precious metals (e.g. rhodium or ruthenium) and complex organic ligands, the elaborate metal and ligand recovery, the frequently low substrate to catalyst loadings and turnover rates, the susceptibility of the reaction to trace catalyst poisons and the need for expensive high pressure reactor equipment, for instance operating at up to 60 bar hydrogen pressure on a large scale.

Provided is a process for the preparation of a compound of the formula I, starting either from commercially available materials or compounds already described in the literature, themselves being prepared easily from commercially available materials. Simple and environmentally compatible reagents and solvents may be used, to afford high overall yields and good purity of the products and that can be performed on an industrial scale.

The compound of the formula I may be obtained by the hydrogenation (reduction) of a compound of the formula III by using diimine as a hydrogenating (reducing) agent. The process results in high yield and good regio- and diastereo-selectivity.

Also provided is a process for preparing a compound of the formula I

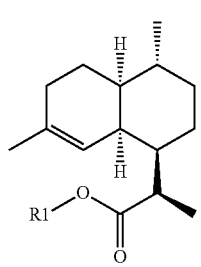

wherein
R1 is hydrogen or linear or branched alkyl having 1, 2, 3, 4, 5 or 6 carbon atoms or cycloalkyl having 3, 4, 5, 6 or 7 carbon atoms,
comprising reacting a compound of the formula III

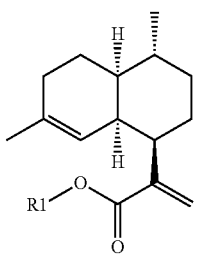

with diimine.
In some embodiments, R1 is hydrogen.
Also provided is a process for preparing a compound of the formula I

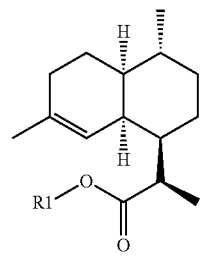

wherein
R1 is linear or branched alkyl having 1, 2, 3, 4, 5 or 6 carbon atoms or cycloalkyl having 3, 4, 5, 6 or 7 carbon atoms, comprising esterifying a compound of the formula IIIa

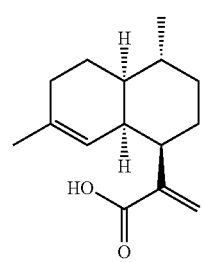

to produce a compound of the formula III

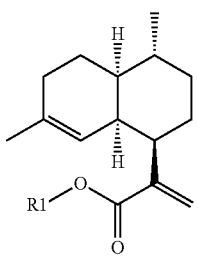

wherein R1 is linear or branched alkyl having 1, 2, 3, 4, 5 or 6 carbon atoms or cycloalkyl having 3, 4, 5, 6 or 7 carbon atoms, and subsequently reacting the compound of the formula III with diimine.

Diimine is a reactive reagent which is also called diimide or diazene and has the chemical formula HN=NH.

In some embodiments, the diimine is generated in situ. Some methods for the preparation of diimine involve (i) the oxidation of hydrazine with an oxidant such as hydrogen peroxide or oxygen, optionally in the presence of a Cu(I) catalyst, (ii) the acid-catalyzed decarboxylation of azodicarboxylate, e.g. decarboxylation of disodium or dipotassium azodicarboxylate with acetic acid, propionic acid, formic acid, tartaric acid, citric acid or oxalic acid, (iii) treating hydroxylamine with an acetic acid ester, e.g. methyl acetate or ethyl acetate, (iv) treating hydroxylamine-O-sulfonic acid with a base, or (v) treating hydroxylamine-O-sulfonic acid and hydroxylamine with a base, e.g. an alkaline or earth alkaline metal hydroxide such as sodium hydroxide or potassium hydroxide, or sodium methylate, sodium ethanolate, potassium methanolate, potassium ethanolate, sodium tert-butoxide, potassium tert-butoxide or an amine like triethylamine, tributylamine or N-methylaniline. Numerous methods for generating diimine are readily available and are, for example, summarized in D. J. Pasto, R. T. Taylor, Organic Reactions, 40, 91-155, 1991.

Optionally, the compound of the formula I can be isolated by methods known in the art, e.g. chromatography or crystallization, which, in some embodiments, may further increase the diastereomeric purity of the product.

Esterification of the compound of the formula IIIa can be performed by a method known in the art, e.g. as described by W. Greene et al.; Protective Groups in Organic Synthesis; Wiley-Interscience $3^{rd}$ ed., chapter 5 (1999). For example, esterification reactions can be performed by the following methods:
(i) by reacting compound IIIa with a compound R1-X, wherein X is F, Cl, Br, or I, and in some embodiments, X is Cl or Br; or
(ii) by reacting compound IIIa with a diazoalkane (e.g., with diazomethane to provide the methylester); or
(iii) by preparing an acid chloride of the formula IIIb from compound IIIa

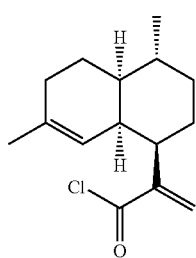

IIIb by methods known in the art, and subsequently reacting the acid chloride with an alcohol of formula R1-OH; or
(iv) by condensation of a compound of the formula IIIa with the respective alcohol of formula R1-OH in the presence of carbonyldiimidazole, a carbodiimide or a chloroformate.

It has been found that artemisinic acid IIIa or its ester derivatives of the general formula III can be hydrogenated (reduced) under mild conditions and in high yield with excellent regio- and diastereoselectivity, without expensive precious metals and ligands by using in situ prepared diimine.

Sufficient quantities of artemisinic acid IIIa are available from several sources, e.g., from plant extraction of Artemisia annua (R. J. Roth et al., Planta Med; 53, 501 (1987)), or from the yeast fermentation process as described by J. D. Keasling et al. (Nature, 440, 940 (2006)). Compounds of the formula III wherein R1 is linear or branched alkyl having 1, 2, 3, 4, 5 or 6 carbon atoms or cycloalkyl having 3, 4, 5, 6 or 7 carbon atoms can be prepared by esterification of artemisinic acid IIIa by methods generally known by persons skilled in the art. For example, X. Xu et al., Tetrahedron 42, 819 (1986), describes the synthesis of artemisinic acid methyl ester (a compound of the formula III wherein R1 is methyl) by reacting artemisinic acid with $CH_2N_2$, for example, in ether at 0° C. Zhou et al. (Huaxue Xuebao 43(9), 845-851, 1985) describes the synthesis of artemisinic acid tert-butyl ester by generating a mixed anhydride of artemisinic acid with pivaloylchloride and treating the product with sodium tert-butanolate. Further examples of procedures for the transformation of acids into esters are provided, for instance in W. Greene et al.; Protective Groups in Organic Synthesis, Wiley-Interscience $3^{rd}$ ed., chapter 5 (1999).

The compound of the formula I can be oxidized to artemisnin of the formula II by methods known in the art, e.g. as described by X. Xu et al. (Tetrahedron; 42, 819 (1986)), R. J. Roth et al. (U.S. Pat. No. 4,992,561) and K. Reiling et al. (WO 2006/128126), i.e. by oxygenation of a compound of the formula I with hydrogen peroxide and sodium molybdate dihydrate, followed by a second oxidation with oxygen in the presence of copper (II) trifluoromethanesulfonate to yield arteminisin of the formula II.

In the compound of the formula I wherein R1 is linear or branched alkyl having 1, 2, 3, 4, 5 or 6 carbon atoms or cycloalkyl having 3, 4, 5, 6 or 7 carbon atoms, the ester compound may be previously cleaved to a compound of the formula I wherein R1 is H by methods known in the art as described by W. Greene et al., Protective Groups in Organic Synthesis, Wiley-Interscience $3^{rd}$ ed., e.g. by reacting the said compound with a base.

Also provided is a process for the preparation of arteminisin of the formula II wherein a compound of the formula IIIa is reacted with diimine to yield a compound of the formula Ia, and subsequently the compound Ia is oxidized to arteminisin of the formula II, as described above.

The following embodiments of the invention comprise procedures for the in situ diimine generation which were found to be useful for the hydrogenation (reduction) process described herein. They are provided by way of illustration and not by way of limitation since those of skill in the art will readily recognize that other experimental procedures are likewise applicable to generate diimine in situ and will give similar results, the detailed reaction conditions being dependent on the method chosen to perform the diimine generation.

Ranges are understood to include all points between and including the specified endpoints. For example, a temperature range of about 15° C. to 25° C. includes each and every temperature between about 15° C. and about 25° C. Likewise a range of time of 1 to 3 hours includes each and every time point between 1 and 3 hours.

In some embodiments, a compound of the formula III is dissolved in water. In some embodiments, when R1 in the compound of the formula III is hydrogen, the compound of formula III is artemisinic acid, the compound of formula IIIa. Optionally, an organic co-solvent chosen from a water-miscible solvent like methanol, ethanol, n-propanol, isopropanol, dioxane, tetrahydrofuran and dimethylformamide may be added. In some embodiments, a low boiling alcohol like methanol, ethanol or isopropanol is added. In some embodiments, methanol or ethanol is added. In some embodiments, a base may be added to adjust the pH value between 4 and 14, such as between 8 and 10. Examples of the base are sodium hydroxide, potassium hydroxide, other alkaline or earth alkaline metal hydroxides, sodium methylate, sodium ethanolate, potassium methanolate, potassium ethanolate, sodium tert-butoxide, potassium tert-butoxide or an amine like triethylamine, tributylamine or N-methylaniline. As an example of the methods available for the formation of diimine, hydroxylamine and hydroxylamine-O-sulfonic acid ($H_2N$—$OSO_3H$, HOSA) are added to the reaction medium while keeping the pH constant at a range between 6 and 14, by addition of at least one of the bases listed above. In some embodiments, the pH is kept constant at a range between 8 and 10. In some embodiments, at least one equivalent or an excess, for example 1.0 to 7.0 equivalents each of hydroxylamine and HOSA are used to perform the process. In some embodiments, the reaction temperature ranges from −60° C. to 120° C. In some embodiments, the reaction temperature ranges from −20° C. to 60° C. The reaction times are variable and depend on the reaction scale, the base, the solvent and the temperature selected for this process. Reaction times may range from 0.5 hours to 24 hours when the reaction temperature ranges from 60° C. to −20° C. The reaction turnover may be controlled by monitoring the reaction, for example using reversed phase high pressure liquid chromatography techniques (RP-HPLC), before submitting the mixture to the work-up procedure. After complete consumption of the substrate, the compound of the formula I obtained by the process can be isolated by methods known to those skilled in the art. These procedures can include an aqueous work-up of the reaction mixture or a chromatography of the reaction mixture. An example of a convenient work-up procedure involves acidifying the reaction mixture, for instance with hydrochloric acid, and then extraction of the desired product of the formula I, for example by a standard extraction with a water immiscible solvent like 2-methyl-tetrahydrofuran, dichloromethane, methyl-tert-butylether (MTBE), toluene, ethyl acetate, heptane, cyclohexane, methyl-isobutylketone, benzene or isobutyl acetate. In some embodiments, the water immiscible solvent is dichloromethane or MTBE. Standard aqueous work-up procedures allow for the isolation of the compound of formula I. Alternatively, the desired product can be obtained by a chromatographic purification or by crystallization. The diastereomeric ratio of the crude products of formulae I:IV that can be achieved by this procedure without crystallization is typically better than 90%:10% and can approach a ratio of 99%:1%. In addition, the diastereomeric purity of the product can be enhanced to 100% by crystallization.

In some embodiments, HOSA is added in portions or continuously to the reaction medium containing a compound of the formula III and a base in a solvent as described below. In some embodiments, the reaction medium contains artemisinic acid IIIa. At least one equivalent or an excess, for example 1.0 to 7.0 equivalents of HOSA is used to perform the process. A base to perform the reaction can be, but is not limited to, sodium hydroxide, potassium hydroxide, other alkaline or earth alkaline metal hydroxides, sodium methylate, sodium ethanolate, potassium methanolate, potassium ethanolate, sodium tert-butoxide, potassium tert-butoxide or an amine like triethylamine, tributylamine or N-methylaniline. In some embodiments, the solvent is water, optionally with the addition of a water-miscible solvent like methanol, ethanol, n-propanol, isopropanol, dioxane, tetrahydrofuran or dimethylformamide. In some embodiments, a low-boiling alcohol like methanol, ethanol or isopropanol is added. In some embodiments, methanol or ethanol is added. The reaction temperature ranges from between 10° C. and 120° C., depending on the boiling temperature of the solvent. In some embodiments, the reaction temperature ranges between 20° C. and the boiling temperature of the solvent, such as aqueous methanol or ethanol, respectively. The reaction time may range between 1 hour and 24 hours when the reaction temperature ranges from 65° C. in methanol to 30° C. in the same solvent. The reaction turnover may be controlled by monitoring the reaction before submitting the mixture to the work-up procedure. After complete consumption of the substrate, as determined by e.g. reversed phase high pressure liquid chromatography techniques (RP-HPLC), the product of the formula I obtained by the process can be isolated with methods as outlined above. The diastereomeric ratio of the crude products of formulae I:IV that can be achieved by this procedure is typically better than 90%:10% for the desired diastereomer and can approach up to 99%:1% or more.

In some embodiments, a compound of the formula III is dissolved in water optionally with the addition of variable amounts of a water-miscible alcoholic solvent like methanol, ethanol, n-propanol or isopropanol. In some embodiments, when R1 in the compound of the formula III is hydrogen, the compound of the formula III is artemisinic acid, e.g., the compound of formula IIIa. In some embodiments, an aqueous hydrogen peroxide solution, for instance a 10% to 70% solution in water, and an aqueous hydrazine hydrate solution, for instance a 64% solution in water, are added simultaneously while keeping the reaction temperature in a range between −40° C. and 80° C. In some embodiments, the reaction temperature is between −20° C. and 40° C. In some embodiments, at least one equivalent or an excess, for example 1.0 to 7.0 equivalents of each hydrazine hydrate and hydrogen peroxide is used to perform the process.

The reaction turnover is controlled by monitoring the reaction, for example by using reversed phase high pressure liquid chromatography techniques (RP-HPLC) before submitting the mixture to the work-up procedure. The diastereomeric ratio of the crude products of formulae I:IV that can be achieved by this procedure is typically better than 90%:10% for the desired diastereomer and can approach up to 99%:1% or more depending on the reaction conditions.

The reaction rates are dependent on the reaction temperature, the solvents and the mixing conditions applied to the reactive components in the reaction medium. Micro-mixing techniques may be useful to achieve advantageous turnover rates of substrates. After complete conversion of the respective substrate, the reaction mixture is diluted with water and with a water-immiscible solvent, for instance MTBE, cyclohexane, methyl-cyclohexane, toluene or any other water-immiscible organic solvent that does not form peroxides with the potentially remaining excess hydrogen peroxide. If some excess hydrogen peroxide is present in the organic phase, it may be destroyed by methods known to those skilled in the art, for example with catalase or by washing with an aqueous iron sulphate solution. The product is then isolated from the organic solution by chromatography or directly by crystallization from solvents or mixtures of solvents like MTBE, heptane, toluene, diisopropylether, ethyl acetate, methanol, ethanol, propanol and water.

In some embodiments, a compound of the formula III is added to a suspension of the disodium or dipotassium salt of azodicarboxylic acid in a solvent such as tetrahydrofuran, 2-methyltetrahydrofuren, toluene, dioxane, isopropanol, tert-butanol, methanol, ethanol, ethyleneglycol-monomethyl ether or ethyleneglycol-dimethylether. In some embodiments, when R1 in the compound of the formula III is hydrogen, the compound of formula III is artemisinic acid, e.g., the compound of formula IIIa. In some embodiments, the solvent is ethanol, methanol or isopropanol. In some embodiments, the diimine is produced in situ in the reaction mixture by decomposing the sodium or potassium salt of azodicarboxylic acid with a weak acid like citric acid, acetic acid, propionic acid, tartaric acid, oxalic acid or formic acid at a reaction temperature from about −10° C. to 100° C., dependent on the solvent used. The reaction times are variable from several minutes to several hours, dependent on the reaction scale and reaction temperature. In some embodiments, at least one equivalent or an excess, for example 1.0 to 7.0 equivalents of the sodium or potassium salt of azodicarboxylic acid is used to perform the process. Reaction monitoring and work-up procedures are the same as outlined above.

In some embodiments, artemisinic acid IIIa is dissolved in dimethylformamide (DMF), N-methylpyrrolidone (NMP), or N,N-dimethylacetamide (DMA) and reacted with a solution containing hydroxylamine and ethyl acetate or methyl acetate in DMF, NMP or DMA. In some embodiments, artemisinic acid IIIa is dissolved in DMF and reacted with a solution containing hydroxylamine and ethyl acetate or methyl acetate in DMF. In some embodiments, the reaction is kept in a range between 20° C. and 120° C. In some embodiments, the reaction is kept in a range between 50° C. and 100° C. In some embodiments, at least one equivalent or an excess, for example 1.0 to 20 equivalents of each hydroxylamine and the acetate ester is used to perform the process. The reaction turnover is controlled by monitoring the reaction, for example by using reversed phase high pressure liquid chromatography techniques (RP-HPLC), before submitting the mixture to the work-up procedure. The diastereomeric ratio of the crude products of formulas Ia:IVa (i.e., the compounds of formula I and IV, respectively, wherein R1 is hydrogen) that can be achieved by this procedure is typically better than 90%:10%. The reaction rates are dependent on the reaction temperature, the solvents and the mixing conditions applied to the reactive components in the reaction medium. In some embodiments, after complete conversion the reaction mixture is acidified for instance with dilute hydrochloric acid and the product is extracted with a water-immiscible solvent, for instance MTBE, cyclohexane, methyl-cyclohexane, or toluene. The product is then conventionally isolated from the organic solution by chromatography or crystallization.

ABBREVIATIONS

DMF dimethylformamide
DMSO dimethylsulfoxide
g gram
h hour
HOSA hydroxylamine-O-sulfonic acid
KOH potassium hydroxide
MHz megahertz
MTBE methyl-tert-butylether
MeOH methanol
Mp melting point
NaOH sodium hydroxide
NMR nuclear magnetic resonance
ppm parts per million
RP-HPLC reversed phase high performance liquid chromatography
TMS tetramethylsilane

EXAMPLES

The following examples are provided by way of illustration only and not by way of limitation. Those of skill in the art will readily recognize a variety of parameters that could be changed or modified to yield similar results.

The NMR assignments are for illustration only based on analysis of the one-dimensional $^1$H-NMR and $^{13}$C NMR spectra as done by those skilled in the art. A more detailed analysis of the spectra may lead to minor reassignments of some NMR peaks, which does not change the overall assignment. All $^1$H-NMR spectra are recorded on a 500 MHz instrument, shifts are relative to TMS in [ppm], and the solvent is DMSO-$d_6$.

In addition to the NMR analysis a HPLC/MS analysis method was used to determine the diastereomeric ratio of the compounds of formulas I and IV:

HPLC analysis experimental conditions:

Column Atlantis T3 length 150 mm*4.6 mm; porosity: 3 µm

Eluent A water with 0.04% v/v of formic acid

Eluent B acetonitrile with 0.05% v/v of formic acid injection 10 µl

Detection 205 nm

Temperature 35° C.

Gradient

| Time (min) | % A | % B | Flow rate (mL/min) |
| --- | --- | --- | --- |
| 0 | 50 | 50 | 1.5 |
| 2 | 50 | 50 | 1.5 |
| 21 | 5 | 95 | 1.5 |
| 25 | 5 | 95 | 1.5 |

Post Time 5 min

Example 1

Synthesis of Dihydroartemisinic Acid Ia by Diimine Generation from HOSA and Sodium Methylate at 65° C. in Methanol 0.248 g (0.001 mol) of artemisinic acid IIIa was dissolved in 10 mL MeOH. Then 0.432 g (0.008 mol) of sodium methylate was added. The reaction mixture was heated to reflux (65° C.) and 0.628 g (0.005 mol) of hydroxylamine-O-sulfonic acid (HOSA) were added in portions. After complete addition the reaction mixture was stirred for additional 1 h at the same temperature until RP-HPLC analysis showed complete consumption of the starting material. The reaction mixture was acidified with diluted aqueous hydrochloric acid to pH 2. The product was extracted with MTBE, dried over magnesium sulfate and the solvent was evaporated to give the 0.22 g (93%) of the title compound which crystallized on standing. The diastereomeric ratio in the unpurified product as determined by $^1$H-NMR and HPLC/MS analysis was >96:4 in favour of the desired stereoisomer Ia.

(2R)-Stereoisomer Ia:

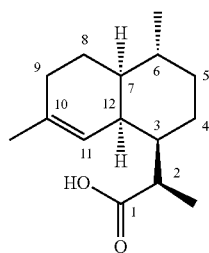

Mp 137-138° C. (lit.: 136-137° C., T. E. Wallaart et al., J. Nat. Prod. 1999, 62, 430-433).

$^1$H NMR (DMSO-d$_6$):

12.0 (s, 1H, OH), 5.14 (s, 1H, H-11), 2.52 (m, 1H, H-2), 2.54 (m, 1H, H-12), 1.95 and 1.84 (m, 2H, H-9), 1.98 and 1.59 (m, 2H, H-8), 1.66 (m, 1H, H-3), 1.46, 1.16 (m, 2H, H-4), 1.65 (s, 3H, 10-Me), 1.63 and 1.00 (m, 2H, H-5), 1.46 (m, 1H, H-6), 1.28 (m, 1H, H-7), 1.22 (d, 2H, 2-Me), 0.89 (d, 3H, 6-Me).

$^{13}$C NMR (DMSO-d$_6$):

184.01 (C-1), 42.24 (C-2), 15.05 (2-Me), 43.55 (C-3), 27.40 (C-4), 35.22 (C-5), 27.65 (C-6), 19.68 (6-Me), 41.71 (C-7), 25.76 (C-8), 26.60 (C-9), 136.00 (C-10), 23.81 (10-Me), 119.29 (C-11), 36.33 (C-12).

(2S)-Stereoisomer IVa:

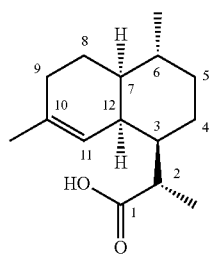

$^1$H NMR (DMSO-d$_6$): 12.0 (s, 1H, OH), 5.33 (s, 1H, H-11)

Example 2

Synthesis of Dihydroartemisinic Acid Ia by Diimine Generation from Hydroxylamine and HOSA in Methanol at 40-50° C.

5.3 g (0.08 mol) of hydroxylamine (50% in water) and 15.1 g (0.12 mol) of HOSA (dissolved in 25 mL of water) were added continuously to a solution of 4.69 g (0.02 mol) of artemisinic acid IIIa in 10 mL MeOH while keeping the pH value constant at pH 9 with an aqueous 5N NaOH solution. The temperature range was between 40° C. and 50° C. After complete addition the reaction mixture was stirred for one additional hour until no pH change was detectable. The complete consumption of artemisinic acid Ia was confirmed with RP-HPLC analysis. Then the reaction mixture was acidified with dilute aqueous hydrochloride acid to pH 2. The product was extracted with MTBE, dried over magnesium sulfate and the solvent was evaporated to give 4.8 g (100%) of the title compound which crystallized on standing. The diastereomeric ratio in the unpurified product as determined by $^1$H-NMR and LC/MS analysis was 96:4 in favour of the title compound.

Example 3

Synthesis of Dihydroartemisinic Acid Ia by Diimine Generation from Hydroxylamine and HOSA/NaOH in Methanol at −5° C. to 0° C.

2.34 g (0.01 mol) of artemisinic acid IIIa was dissolved in 20 mL of MeOH. Then 1.98 g (0.03 mol) of hydroxylamine (50% in water) and 5.65 g (0.045 mol) of HOSA (dissolved in 10 mL of water) were added continuously while a pH 9 was held maintained with a 32% aqueous NaOH solution. The temperature was adjusted to between −5° C. and 0° C. After complete addition the reaction mixture was stirred for one additional hour until no pH change was detectable. The complete consumption of artemisinic acid was confirmed with RP-HPLC analysis. Then the reaction mixture was acidified with dilute aqueous hydrochloride acid to pH 2. The product was extracted with MTBE, dried over magnesium sulfate and the solvent was evaporated to give 2.25 g (95%) of the title compound which crystallized on standing. The diastereomeric ratio in the unpurified product as determined by $^1$H-NMR and LC/MS analysis was 98:2 in favour of the desired stereoisomer Ia.

Example 4

Synthesis of Dihydroartemisinic Acid Ia by Diimine Generation from Hydroxylamine and Ethyl Acetate 6.95 g (0.1 mol) of hydroxylamine hydrochloride was suspended in 10 mL of DMF and 6.60 g of powdered KOH was added. After 10 min at 30° C. the suspension was filtered and the filtrate containing hydroxylamine was collected. Under cooling with an ice bath 3.19 g (0.044 mol) of ethyl acetate was added to the hydroxylamine solution. This solution was then added dropwise to a solution of 0.47 g (0.002 mol) of artemisinic acid IIIa dissolved in 10 mL of DMF at 90° C. After complete addition the reaction mixture was stirred for one additional hour until complete consumption of artemisinic acid was confirmed by RP-HPLC analysis. Then the reaction mixture was acidified with diluted aqueous hydrochloric acid to pH 2. The product was extracted with MTBE, dried over magnesium sulfate and the solvent was evaporated to give 0.36 g (76%) of the crude product which crystallized after column chromatography (silica gel, 1:2 ethyl acetate: heptane as eluent) to give 0.26 g (55%) of the purified title compound. The diastereomeric ratio in the unpurified crude reaction product as determined by $^1$H-NMR and LC/MS analysis was 95:5 in favour of the desired stereoisomer Ia.

Example 5

Synthesis of Dihydroartemisinic Acid Ia by Diimine Generation from Hydroxylamine and HOSA/KOH 0.248 g (0.001 mol) of artemisinic acid IIIa was dissolved in 5 mL MeOH. Then 2.24 g (0.02 mol) of KOH (50% in water) was added. The reaction mixture was heated to 40° C. and 0.264 g (0.004 mol) of hydroxylamine and 0.754 g (0.006 mol) of HOSA acid were added simultaneously in portions. After complete addition the reaction mixture was stirred for one additional hour at the same temperature until RP-HPLC analysis confirmed the complete consumption of the starting material. Then the reaction mixture was acidified with dilute aqueous hydrochloride acid to pH 2. The diastereomeric ratio in the unpurified crude reaction product as determined by ¹H-NMR and LC/MS analysis was 95:5 in favour of the desired stereoisomer.

Example 6

Synthesis of Dihydroartemisinic Acid Ia by Diimine Generation from Hydrazine and Hydrogen Peroxide To an ice-cooled solution of 0.248 g (0.001 mol) of artemisinic acid IIIa in 2 mL of absolute EtOH and 0.821 g (0.0105 mol) of hydrazine hydrate (64% in water) was added 0.641 mL (0.0063 mol) of a 30% aqueous hydrogen peroxide solution during 1 h. After complete addition the reaction mixture was warmed up to room temperature and stirred for additional 4 h until RP-HPLC analysis confirmed the complete consumption of the starting material. Then the mixture was acidified with dilute aqueous hydrochloric acid to pH 2, the product was extracted with MTBE, washed once with a $FeSO_4$-solution and brine and dried over magnesium sulphate. The solvent was evaporated to give 0.222 g (93%) of the crystalline title compound. The diastereomeric ratio in the unpurified product as determined by ¹H-NMR and LC/MS analysis was 95:5 in favour of the desired stereoisomer Ia.

Example 7

Large Scale Synthesis of Dihydroartemisinic Acid Ia by Diimine Generation from Hydroxylamine and HOSA 11.72 g (0.05 mol) of artemisinic acid IIIa was dissolved in 25 mL of hot (about 50° C.) MeOH. The pH was adjusted to 9 with a 32% solution of NaOH in water. 13.2 g (0.2 mol) of hydroxylamine (50% solution in water) and 25.1 g (0.2 mol) of HOSA (dissolved in 30 mL of water) were added simultaneously while a pH 9 was maintained with the 32% solution of NaOH in water. The internal temperature range was kept between −5° C. and 5° C. by cooling. After complete addition the reaction mixture was stirred for one additional hour until the pH remained constant. The complete consumption of artemisinic acid IIIa was confirmed by with RP-HPLC analysis. A total volume of approximately 30 mL of NaOH (~6.5 equiv) was consumed. Then the reaction mixture was acidified with dilute aqueous hydrochloric acid to pH 2. The product was extracted with 100 mL of MTBE, washed once with 25 mL of water and dried over magnesium sulfate. The solvent was evaporated to give 11.1 g (93%) of the crystalline title compound. NMR analysis revealed MTBE as an impurity. The diastereomeric ratio was assessed by ¹H-NMR analysis to be >97:3 in favour of the desired title compound. This material was further purified as follows: 11 g of the crude product was dissolved in 12 mL of refluxing ethanol and 6 mL of water was added in the heat. Slow cooling generated crystals which were filtered off after stirring 30 min in an ice-cooled bath. The filter cake was washed once with ice cooled 20 mL of ethanol/water (1/1) followed by 30 mL of water. Drying generated 9.0 g (76%) of the desired product Ia whereas the undesired diastereomer was below the limit of detection by the NMR and HPLC methods applied.

Example 8

Synthesis of Dihydroartemisinic Acid Ia by Diimine Generation from Dipotassium Azodicarboxylate To a stirred solution of 4.22 g (0.035 mol) of KOH (40% in water) at 5° C. was added 0.500 g (0.0043 mol) of azodicarbamide in small portions. After stirring for an additional hour the bright yellow solid which precipitated was filtered off and washed several times with cold methanol to give 0.683 g (80%) of the dipotassium azodicarboxylate. This salt and 0.234 g (0.001 mol) of artemisinic acid IIIa were suspended in 5 mL of absolute methanol. Under stirring and cooling with an ice bath, a solution of 0.36 g (0.006 mol) of acetic acid in 1 mL of absolute methanol was added dropwise within 30 min. After stirring for 4 hours at room temperature, water and MTBE were added, the organic phase was washed once with 10 mL of 1M aqueous HCl and dried over magnesium sulphate. Evaporation of the solvent gave 0.23 (97%) of the crystalline title compound. The diastereomeric ratio in the unpurified product as determined by ¹H-NMR and LC/MS analysis was 97:3 in favour of the desired stereoisomer Ia.

Example 9

Synthesis of Dihydroartemisinic Acid Methyl Ester (Compound I Wherein R1=Methyl) by Diimine Generation from Hydrazine and Hydrogen Peroxide To an ice-cooled solution of 0.248 g (0.001 mol) of artemisinic acid methyl ester (compound III wherein R1=methyl), prepared by a literature procedure (X. Xu et al., Tetrahedron 42, 819 1986), in 2 mL of absolute ethanol and 0.821 g (0.0105 mol) of hydrazine hydrate (64% solution in water) were added 0.641 mL (0.0063 mol) of an aqueous 30% hydrogen peroxide solution during 1 h. After complete addition the reaction mixture was warmed up to room temperature and stirred for additional 4 h until RP-HPLC analysis showed the complete consumption of the starting compound. The reaction mixture was acidified with diluted aqueous hydrochloride acid to pH 2, the product was extracted with MTBE, washed once with a $FeSO_4$-solution and brine, dried over magnesium sulphate and evaporated to give 0.222 g (93%) of the title compound. The diastereomeric ratio as determined by ¹H-NMR and LC/MS analysis was 97:3 in favour of the desired compound.

¹H NMR (DMSO-$d_6$): 5.15 (s, 1H, H-11), 3.60 (s, 3H, 10-Me), 1.62 (s, 3H, 10-Me), 1.05 (d, 2H, 2-Me), 0.84 (d, 3H, 6-Me); the corresponding signals for the minor isomer appear at 5.25 (s, 1H, H-11), 3.59 (s, 3H, OMe).

Example 10

Synthesis of Dihydroartemisinic Acid Tert-Butyl Ester (Compound I Wherein R1=Tert-Butyl) by Diimine Generation with Hydrazine and Hydrogen Peroxide To an ice-cooled solution of 0.290 g (0.001 mol) of artemisinic acid tert-butyl ester (compound III wherein R1=tert-butyl), prepared by a literature procedure (W. Zhou et al., Huaxue Xuebao 43(9), 845-851, 1985), in 2 mL of absolute ethanol and 0.821 g (0.0105 mol) of hydrazine hydrate (64% solution in water) were added 0.641 mL (0.0063 mol) of an aqueous 30% hydrogen peroxide solution during 1 h. After complete addition the reaction mixture was warmed up to room temperature and stirred for additional 4 h until RP-HPLC analysis showed the complete consumption of the starting compound. The reaction mixture was acidified with diluted aqueous hydrochloride acid to pH 2, the product was extracted with MTBE, washed once with a $FeSO_4$-solution and brine, dried over magnesium sulphate and evaporated to give 0.290 g (98%) of the title compound.

¹H NMR (DMSO-d₆): 5.14 (s, 1H, H-11), 1.58 (s, 3H, 10-Me), 1.44 (s, 9H, t-Bu), 1.02 (d, 2H, 2-Me), 0.88 (d, 3H, 6-Me).

What is claimed is:

1. A process for the preparation of a compound of the formula I

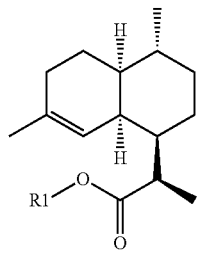

wherein R1 is hydrogen or linear or branched alkyl having 1, 2, 3, 4, 5 or 6 carbon atoms or cycloalkyl having 3, 4, 5, 6 or 7 carbon atoms,
comprising reacting a compound of the formula III

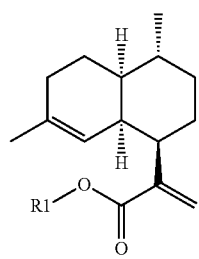

with diimine, wherein the diimine is prepared in situ.

2. A process as claimed in claim 1 wherein the diimine is generated from hydroxylamine and hydroxylamine O-sulfonic acid in the presence of a base.

3. A process as claimed in claim 1 wherein the diimine is generated from hydroxylamine-O-sulfonic acid in the presence of a base.

4. A process as claimed in claim 1 wherein the diimine is generated from hydroxylamine and an acetic acid ester.

5. A process as claimed in claim 1 wherein the diimine is generated from hydrazine and an oxidant.

6. A process as claimed in claim 1 wherein the diimine is generated from acid-catalyzed decarboxylation of azodicarboxylate.

7. A process according to any of claims 1 or 2 to 6, further comprising oxidizing the compound of the formula I to artemisinin II

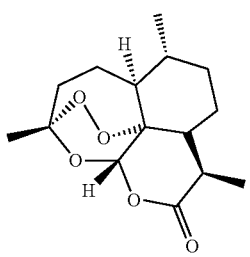

* * * * *